US009415141B2

(12) United States Patent
Kudryavtseva et al.

(10) Patent No.: US 9,415,141 B2
(45) Date of Patent: Aug. 16, 2016

(54) METHOD FOR MAKING BIODEGRADABLE ANTI-ADHESION MEMBRANES FOR CARDIAC SURGERY

(71) Applicant: Federal State Budgetary Institution Research Institute for Complex Issues of Cardiovascular Diseases (NII KPSSZ), Kemerovo (RU)

(72) Inventors: Yuliya A. Kudryavtseva, Kemerovo (RU); Marina V. Nasonova, Kemerovo (RU); Leonid S. Barbarash, Kemerovo (RU)

(73) Assignee: Federal State Budgetary Institution Research Institute for Complex Issues of Cardiovascular Diseases (NII KPSSZ), Kemerovo (RU)

(*) Notice: Subject to any disclaimer, the term of this patent is extended or adjusted under 35 U.S.C. 154(b) by 0 days.

(21) Appl. No.: 14/926,470

(22) Filed: Oct. 29, 2015

(65) Prior Publication Data
US 2016/0045643 A1 Feb. 18, 2016

Related U.S. Application Data

(63) Continuation of application No. PCT/RU2014/000533, filed on Jul. 21, 2014.

(30) Foreign Application Priority Data

Jul. 26, 2013 (RU) ................................ 2013135289

(51) Int. Cl.
*A61L 31/14* (2006.01)
*A61L 31/04* (2006.01)
*A61L 31/16* (2006.01)
*A61P 41/00* (2006.01)
*A61L 31/06* (2006.01)

(52) U.S. Cl.
CPC ............... *A61L 31/06* (2013.01); *A61L 31/041* (2013.01); *A61L 31/148* (2013.01); *A61L 31/16* (2013.01); *A61L 2300/42* (2013.01)

(58) Field of Classification Search
CPC ......... A61L 31/06; A61L 31/16; A61L 31/48; A61L 2300/42
USPC ...................................................... 514/772.3
See application file for complete search history.

(56) References Cited

U.S. PATENT DOCUMENTS 7,943,683 B2  5/2011  Rizk et al.

FOREIGN PATENT DOCUMENTS

RU    2177332 C2   12/2001
RU    2447902 C2    4/2012
WO    2011/121858 A1  10/2011

OTHER PUBLICATIONS

International Search Report from International Application No. PCT/RU2014/000533 filed Jul. 21, 2014, mailed Oct. 30, 2014.

Walther T. et al, A novel adhesion barrier facilitates reoperations in complex congenital cardiac surgery, The Journal of Thoracic and Cardiovascular Surgery, Feb. 2005, pp. 359-363, vol. 129.
Klingler P. J. et al, Seprafilm-induced peritoneal inflammation: a previously unknown complication, Dis Colon Rectum, Dec. 1999, pp. 1639-1643, v. 42. No. 12.
Lodge A. J. et al. A Novel bioresorbable film reduces postoperative adhesions after infant cardiac surgery, Ann. Thorac. Surg., 2008, pp. 614-621, v. 86, Elsevier Inc.
Gogolewski, S. et al, Tissue response and in vivo degradation of selected polyhydroxyacids: Polylactides (PLA) poly(3-hydroxybutyrate) (PHB), and poly(3-hydroxybutyrate-co-3-hydroxyvalerate) (PHB/VA), Journal of Biomedical Materials Research, 1993, pp. 1135-1148, vol. 27, John Wiley & Sons, Inc.
Chaput, C. et al, Processing biodegradable natural polyesters for porous soft-materials, Advances in Materials Science and Implant Orthopedic Surgery, 1995, pp. 229-245, Kluwer Academic Publishers.
Qu, X.-H. et al, In vivo studies of poly(3-hydroxybutyrate-co-3-hydroxyhexanoate) based polymers: Biodegradation and tissue reactions, Biomaterials, 2006, pp. 3540-3548, v. 27, Elsevier.
Qin et al, Use of Polylactic Acid/Polytrimethylene Carbonate Blends Membrane to Prevent Postoperative Adhesions, Journal of Biomedical Materials Research Part B: Applied Biomaterials, 2006, pp. 312-319, Wiley Periodicals, Inc.
Haensig et al, Bioresorbable Adhesion Barrier for Reducing the Severity of Postoperative Cardiac Adhesions: Focus on REPEL-CV, Medical Devises: Evidence and Research, 2011, pp. 17-25, v. 4, Dovepress.
Walther et al, A novel adhesion barrier facilitates reoperations in complex congenital cardiac surgery, The Journal of Thoracic and Cardiovascular Surgery, 2005, pp. 359-363, v. 129, No. 2.
Replogle, et al, Prevention of Postoperative Intestinal Adhesions with Combined Promethazine and Dexamethasone Therapy: Experimental and Clinical Studies, Annals of Surgery, Apr. 1966, pp. 580-588, v. 163, No. 4.
Iliopoulos, et al, Evaluation of Bioabsorable Polylactide Film in a Large Animal Model for the Reduction of Retrosternal Adhesions, Journal of Surgical Research, May 15, 2004, pp. 144-153, v. 118, No. 2, Elsevier Inc.
Manganas, Reduction of Pericardial Adhesions using a Bioresorbable Membrane, A Thesis Presented for the Degree of Master of Surgery at the Unviersity of New South Wales, Mar. 2010, pp. 1-56, Sydney.
Naito et al, A novel method to reduce pericardial adhesion: A combination technique with hyaluronic acid biocompatible membrane, The Journal of Thoracic and Cardiovascular Surgery, Apr. 2008, pp. 850-856, vol. 135, No. 4.

*Primary Examiner* — Kristin Vajda

(74) *Attorney, Agent, or Firm* — Patentbar International, P.C.

(57) ABSTRACT

A method for the manufacture of biodegradable membranes for preventing adhesion formation followed open heart surgery is described herein. The manufacturing of biodegradable membranes is based on polymeric composition, comprised of copolymer of polyhydroxybutyrate/hydroxyvalerate (PHBV), poly (D, L-lactide) in the ratio of the dried powders of 3:1, the resulting mixture is dissolved in chloroform to a concentration of 6-9% followed by thorough mixing for 2 hours and heating up to 35° C. The membrane is produced by electrostatic spinning (electrospinning), wherein biologically active substances from fibrinolytic agents or direct anticoagulants are embedded in the structure of the fiber.

2 Claims, No Drawings

METHOD FOR MAKING BIODEGRADABLE ANTI-ADHESION MEMBRANES FOR CARDIAC SURGERY

RELATED APPLICATIONS

This Application is a Continuation application of International Application PCT/RU2014/000533, filed on Jul. 21, 2014, which in turn claims priority to Russian Patent Applications No. RU 2013135289, filed Jul. 26, 2013, both of which are incorporated herein by reference in their entirety.

FIELD OF THE INVENTION

The present invention generally relates to medicine, in particular to cardiovascular surgery, and can be used for preventing adhesion formation after open heart surgery.

BACKGROUND OF THE INVENTION

Adhesion formation is a common complication of cardiovascular surgery, affecting sternal reentry in secondary cardiac surgery and causing other significant complications. The prevention of postsurgical adhesion formation is one of the key elements in addressing this challenge, since adhesions prolong operative time, increase the rates of postoperative complications, and cause heavy bleedings.

In-hospital mortality rate following sternal reentry is 14-15%, whereas for emergency surgery –43%. Fatal hemorrhage occurs in 2-6% of all cases. Various methods with different mechanisms of action, application techniques and efficiency are used to prevent adhesion formation. An ideal method for cardiac surgery is an application of a membrane serving as a temporary barrier, that limits the apposition of sternum and pericardium.

The application of biodegradable membranes composed of natural polymers can effectively prevent the formation of adhesions between opposing wound surfaces during the critical period of healing followed by the membrane's biodegradation to non-toxic products.

The antiadhesion membrane "CV Seprafilm" composed of carboxymethylcellulose and sodium hyaluronate is disclosed by Walter T. et al. (A novel adhesion barrier facilitates reoperations in complex congenital cardiac surgery"/Walther T, Rastan A//The Journal of Thoracic and Cardiovascular Surgery. 2005. Vol. 129, Is. 2.-P. 359-363.)

The employment of such membranes have reduced the rate of postoperative adhesion formation in over 50% of patients. However, the prior art discussed above has met with only limited success as it is less efficient in the presence of blood, particularly in excessive bleedings during open heart surgery or great blood vessel repairs.

Additionally, aggravation of postoperative inflammatory responses induced by "Seprafilm" barriers was reported in the medical literature (Seprafilm-induced peritoneal inflammation: a previously unknown complication/Klingler P J, Floch N R, Seelig M H et al/Report of a case//Dis Colon Rectum-1999.-V. 42.-N. 12.-P. 1639-1643).

Of particular interest are the biodegradable barriers "Repel-CV", composed of polylactic acid and polyethylene glycol, that are disclosed by Andrew J. L. et al. (Andrew J. L. et al. A Novel bioresorbable film reduces postoperative adhesions after infant cardiac surgery//The Annals Thorac Surg, 2008; V. 86 (2): P. 614-621). These polymers are widely used to fabricate implants and bioresorbable medical devices.

However, the results of the randomized clinical trial assessing the efficiency of "Repel-CV" adhesion barriers reported 21% failure in the studied cohort who had demonstrated severe adhesion formation and a few cases of mediastinitis. Additionally, hydrolysis of polylactic acid polymer chain in vivo is accompanied with the release of lactic acid, provoking significant tissue acidification (pH increases up to 3.2-3.4) and inducing inflammatory tissue response.

Also of interest are antiadhesion membranes composed of polymer belonging to a larger class of materials called polyhydroxyalkanoates (PHAs) that are produced by numerous microorganisms—poly-4-hydroxybutyrate (PHB), dissolved either in 1,4 dioxane, or tetrahydrofuran, that is disclosed in U.S. Pat. No. 7,943,683, IPC C08G63/06, B29C47/00, publ. May 17, 2011. High biocompatibility of polyhydroxyalkanoates is associated with 3-hydroxybutyric acid, that is a normal metabolite of animal and human cells and tissues.

Due to its high biocompatibility, PHB is used as a raw material for the production of absorbable surgical sutures, osteosynthesis devices, surgical plates, and antiahesion membranes. The main disadvantages of the membrane bathers composed of PHB monopolymer are their insufficient elasticity and excessive fragility that may limit the optimal placement of the membrane into the surgical wound, and may cause the failure of the suture—memebrane interface.

In addition, monopolymer dissolution in solvents is accompanied with the release of highly toxic substances, which may form an explosive mixture when it combines with oxygen.

The closest prior invention is a polymeric film composed of 3-hydroxybutyrate and 3-hydroxyvalerate (PHB-3/3-PGV) dissolved in chloroform and loaded with antibiotics or non-steroidal anti-inflammatory drugs, that is disclosed in RU Pat. No 2447902, A61L31 IPC/08 A61L31/10 A61L31/16.

The employment of polyhydroxybutyrate-hydroxyvalerate copolymer increases the elasticity of the present membranes, compared to those, composed of polyhydroxybutyrate monopolymer. The use of chloroform as a solvent allows minimizing toxic effect.

The main disadvantage in using these antiadhesion membranes is long term biodegradation rate—over three months. The biodegradation rate of membranes for preventing adhesion formation should not exceed 60 days, since adhesions commonly develop between tissue surfaces within 30 days after surgery according to the phases of adhesion genesis. Therefore, long-term employment of antiadhesion bathers in the surgical wound is not recommended as it may provoke the immune response to foreign body.

SUMMARY OF THE INVENTION

The technical result of the present invention guarantees the improvement of hemo- and biocompatibility, the improvement of physical and chemical properties by increasing membrane's elasticity, as well as the optimization of biodegradation rate in the presence of blood cells and particles for preventing adhesion formation during open cardiac surgeries.

The technical result is achieved by the inclusion of poly (D, L-lactide) in the polymer composition to ensure the reduction of biodegradation rate; the membrane is produced using an electrostatic spinning (electrospinning), that allows forming microfibril structure of the present invention and reduce its biodegradation rate.

Moreover, electrospun fibers of the present membrane are loaded with biologically active substances, such as fibrinolytic agents or direct anticoagulant agents, which are released by the biodegradation of the membrane and produce sustained topical effects.

DETAILED DESCRIPTION OF THE INVENTION

In this embodiment the present invention provides a method of making a biodegradable antiadhesion membrane for preventing adhesion formation following cardiac surgery, comprising of dissolution of polyhydroxybutyrate/hydroxyvalerate (PHBV) copolymer in a solvent followed by the incorporation of biologically active substances.

The present invention described hereinabove differs from prior arts by the inclusion of both poly (D, L-lactide) into the composition of the biopolymer in the ratio 3:1 and biologically active substances, fibrinolytic agents, such as fibrinolysin, streptokinase, streptodekaza and alteplase, or direct anticoagulants, such as unfractionated heparin, enoxaparin sodium, dalteparin and nadroparin.

The membrane is produced by electrostatic spinning, which allows fabricating a nonwoven fabric membrane, wherein biologically active substances are incorporated into microfibers. The method of electrostatic spinning generates the microsized structure of the membrane which ensures a faster biodegradation compared to the film membranes.

The electrostatic spinning methods enable the embedding of biologically active substance into the polymeric microfibers, which are subsequently released during the degradation of the membrane and produce prolonged topical therapeutic effects.

Since adhesion formation is a result of decreased fibrinolytic activity of an organism, or a consequence of fibrin deposition in the surgical wound, the use of biologically active substances from fibrinolytic agents will produce topical fibrinolytic effects.

The use of direct anticoagulants inhibits the formation of fibrin and produces anti-inflammatory effects, which will generally prevent adhesion formation. Thus, the biodegradable polymeric membrane composed of (PHBV+poly (D, L-lactide)) serves as a physical barrier between the injured tissue surfaces for a period not exceeding 60 days after the surgery, wherein its degradation is accompanied with the release of active agents that provide topical therapeutic effects.

The comparative studies have proved that the strength of the electrospun PHBV+poly (D, L-lactide) membrane samples is similar to the strength of the native pericardium, to which the membrane is sutured during the surgery, wherein the elasticity of the electrospun membrane is 20% higher than that the membranes, produced by the solvent casting method. The obtained results are presented in Table 1.

TABLE 1

Physical and mechanical properties of membranes

| Membrane composition | Membrane thickness, mm | Strength (MPa) | Relative extension (%) |
|---|---|---|---|
| PHBV produced by the solvent casting method | 0.1 | 19.31 ± 4.85 | 501.5 ± 58.78 |
| PHBV, produced by electrospinning | 0.05 | 6.79 ± 3.54 | 612.7 ± 42.64 |
| PHBV + poly (D, L-lactide), produced by electrospinning | 0.05 | 16.25 ± 5.64 | 604.98 ± 29.79 |

The hemocompatibility of the membrane was evaluated by quantifying the degree of hemolysis induced by aqueous extract. PHBV copolymer membranes produced by both the solvent casting method and electrospinning have not affected the erythrocytes, since the samples showed no evidence of hemolysis.

The structure of PHBV+poly (D, L-lactice) membrane was assessed using scanning electron microscopy. Electrospun membranes exhibited a randomly arranged architecture, wherein the fiber has a diameter of 3.2-3.6 micron. The incorporation of biologically active materials reduces the thickness of the fiber to 1.7-1.9 microns.

The polymer-tissue interaction was evaluated using a rat subcutaneous implantation model. Following the implantation, a thin connective tissue capsule is formed around the implant. This finding is consistent with those of other in literature data (Gogolewski et al, 1993, Chaput et al, 1995, Qu et al, 2006). There were no signs of inflammation in all samples.

The experimental study on the biodegradable properties of the membranes in vivo reported that solution cast membranes, surgically implanted in rat subcutaneous tissue, fully degraded at the end of a 6-month period. Whereas electrospun membranes fully degraded within 60 days after the implantation without signs of lymphocytic infiltration. The incorporation of poly (D, L-lactide) into the membrane composition allowed reducing its biodegradation rate by 30%. 45 days after the implantation, empty chambers were visualized without residues of the membrane.

The efficiency of the present invention for preventing adhesion formation was assessed a laboratory animal model. Male Wistar rats, weighing 250-300 g, were used to create the adhesion model, since rats have a high level of fibrinolytic activity compared to other laboratory animals. The presence and severity of adhesion process were assessed 28 days after the surgery (Table 2).

According to the data presented in Table 2, electrospun membranes have effectively prevented adhesion formation in 65% of cases, and only 5% of rats had extensive and dense adhesions. The embedding of biologically active substances in the present membrane contributes to more efficient prevention of adhesion formation. There were no adhesions in 85% of rats, and 15% of rats demonstrated weak adhesions.

TABLE 2

The efficiency of antiadhesion membranes according to the manufacturing method

| Manufacturing Method | number of animals, undergoing surgery | number of animals with adhesions | % | including extensive and dense adhesions | % |
|---|---|---|---|---|---|
| membrane produced by the solvent casting method | 20 | 10 | 50 | 6 | 30 |
| membrane produced by electrospinning | 20 | 7 | 35 | 1 | 5 |
| Membrane, produced by electrospinning + embedded with biologically active substances | 20 | 3 | 15 | 0 | 0 |

DETAILED DESCRIPTION OF THE PREFERRED EMBODIMENTS

The method for manufacturing biodegradable membrane includes the following steps: the dried powder samples of 3 PHB/3-PGV and poly (D, L-lactide) in the ratio of 3:1 are dissolved in chloroform to a concentration of 6-9%, thorough mixed for 2 hours on a magnetic stirrer with heating up to 30-35° C.

The resulting polymer solution is transferred into a dispensing syringe, mounted in the electrostatic spinning apparatus. Biologically active substance are placed into the second dispensing syringe. The fiber is formed using a coaxial nozzle, which allows forming polymeric fiber and embedding it with biologically active substances.

The fiber is formed at 18-23 kV voltage with the flow rate of polymer and biologically active agents ranging from 0.4 mL/h to 1 mL/h. The size of the membranes ranges from 13×13 cm to 15×18 cm with the thickness from 150 to 500 microns. The membranes are sterilized with ethylene oxide treatment at room temperature.

Thus, electrospun biodegradable membranes based on polyhydroxybutyrate/hydroxyvalerate and poly (D, L-lactide) copolymer with biologically active substances from fibrinolytic agents or direct anticoagulants incorporated into the microstructure, have satisfactory biocompatible properties with biodegradation rate <60 days and effectively prevent adhesion formation in the experimental study.

What is claimed is:

1. A method for manufacturing a biodegradable membrane for preventing adhesion formation after cardiac surgery, the method comprising:

dissolving a polyhydroxybutyrate/hydroxyvalerate (PHBV) copolymer in chloroform to form a composition;

adding at least one biologically active substance to the composition;

adding poly (D, L-lactide) to the composition and further dissolving the composition in the chloroform up to a concentration of 6% to 9%; and stirring the composition for about 2 hours using a magnetic stirrer at a temperature up to 35° C., wherein a ratio of dry PHBV copolymer and dry poly (D, L-lactide) in the composition is 3:1, and wherein the membrane is produced by electrostatic spinning.

2. The method of manufacturing a biodegradable membrane according to claim 1, wherein the at least one biologically active substance is selected from fibrinolytic agents or direct anticoagulants.

* * * * *